United States Patent [19]

Hageman et al.

[11] Patent Number: 4,584,302

[45] Date of Patent: Apr. 22, 1986

[54] METHODS FOR THE TREATMENT OF VENTRICULAR DYSRHYTHMIA AND PREVENTION OF VENTRICULAR FIBRILLATION

[75] Inventors: William E. Hageman, Telford; Michael J. Zelesko, North Wales, both of Pa.

[73] Assignee: McNeilab, Inc., Fort Washington, Pa.

[21] Appl. No.: 535,476

[22] Filed: Sep. 26, 1983

[51] Int. Cl.$^4$ .................. A61K 31/445; A61K 31/40
[52] U.S. Cl. .................................. 514/324; 514/414; 514/422
[58] Field of Search .............................. 424/274, 267

[56] References Cited

U.S. PATENT DOCUMENTS 4,059,583 11/1977 McComsey et al. ............ 260/256.5

OTHER PUBLICATIONS

W. E. Hageman, Archives Internationals de Pharmacodynamie et de Therapie, vol. 237, No. 2 (1979).
Journal of Medicinal Chemistry, 1983, 28,230, M. J. Zelesko.

Primary Examiner—Frederick E. Waddell
Attorney, Agent, or Firm—David J. Levy

[57] ABSTRACT

Various indole and benzothiophene compounds having a pendant pyrrolidinylidene amino or piperidinylideneamino group are useful in the prevention of ventricular fibrillation, e.g., in humans. The invention comprises methods for the treatment of ventricular dysrhythymia or the prevention of ventricular fibrillation.

13 Claims, No Drawings

METHODS FOR THE TREATMENT OF VENTRICULAR DYSRHYTHMIA AND PREVENTION OF VENTRICULAR FIBRILLATION

At present, few methods exist for the treatment of ventricular dysrhythmia and for the prevention of ventricular fibrillation. Ventricular fibrillation in humans results in death unless the heart is defibrillated within 7 to 8 minutes. Bretylium is available to suppress ventricular fibrillation and ventricular arrhythmias but causes catecmolamine release upon initial administration which adversely elevates blood pressure and may make the heart more excitable and prone to fibrillation. Bretylium is not active when administered orally.

It has been observed that various compounds may show activity against either atrial or ventricular arrhythmias while exhibiting little or no activity against the other, see W. E. Hageman et al., in Archives Internationales De Pharmacodynamie et de Therapie, Vol. 237, No. 2, pages 298 to 315 (1979). In particular, compounds which are shown to correct acetylcholine-induced atrial fibrillation may not be active against the more serious ventricular fibrillation caused by ischemia, i.e., loss of oxygen, in the heart muscle. Compounds which are active against atrial arrhythmia as shown in an atrial antiarrhythmia test using acetylcholine are described at columns 9 and 10 of U.S. Pat. No. 4,059,583.

SUMMARY OF THE INVENTION

It has been found that particular indole and benzothiophene compounds increase the resistance of the heart to ventricular fibrillation (also known as "sudden unexpected death") and normalize the beating of the heart. The compounds can be given to patients who have experienced a myocardial infarction (also known as a "heart attack"), an episode of ventricular fibrillation or a history of abnormal cardiac conduction.

DETAILED DESCRIPTION OF THE INVENTION

The compounds to be administered are those of the following formulae (I) through (VIII):

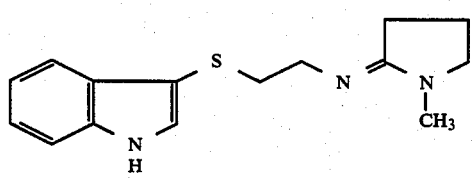

(I)

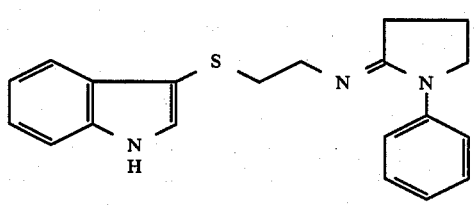

(II)

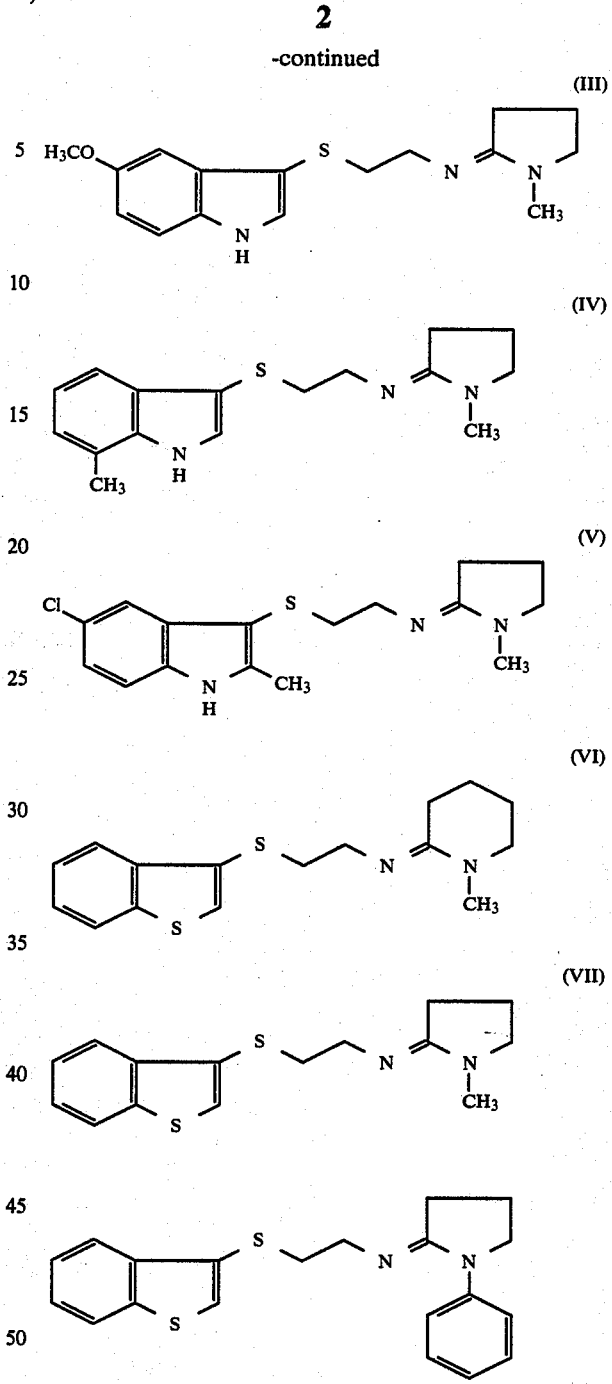

which are named as follows:
3-[2-(1-methyl-2-pyrrolidinyllideneamino)ethylthio]indole (I);
3-[2-(1-phenyl-2-pyrrolidinylideneamino)ethylthio]indole (II);
5-methoxy-3-[2-(1-methyl-2-pyrrolidinylideneamino)ethylthio]indole (III);
3-[2-(1-methyl-2-pyrrolidinylideneamino)ethylthio]-7-methylindole (IV);
5-chloro-3-[2-(1-methyl-2-pyrrolidinylideneamino)ethylthio]-2-methylindole (V);
2-[(3-benzo[b]thienyl)thio]-N-(1-methyl-2-piperidinylidene)ethanamine (VI);
2-[(3-benzo[b]thienyl)thio]-N-(1-methyl-2-pyrrolidinylidene)ethanamine (VII);

2-[(3-benzo[b]thienyl)thio]-N-(1-phenyl-2-pyrrolidinylidene)ethanamine (VIII).

Representative salts of the above compounds which may be used in the processes of the invention include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicylic, p-aminosalicylic, 2-phenoxybenzoic, 2-acetoxybenzoic or a salt made with saccharin.

The 2-(substituted-ethylthio)indoles of the formulae (I) through (V) used in the process of the present invention may be prepared as described in U.S. Pat. No. 4,059,583 which is hereby incorporated by reference. The 2-(substituted-ethylthio)benzothiophenes of the formulae (VI) through (VIII) may be prepared by reacting 3-thianaphthenethioethylamine with N-methyl-2-piperidone, N-methyl-2-pyrrolidinone, or N-phenyl-2-pyrrolidinone, respectively, under conditions described for the corresponding reactions of 3-[(2-aminoethyl)thio]indoles in U.S. Pat. No. 4,059,583. The 3-thianaphthenethioethylamine intermediate is prepared by reacting thianaphthene with sulfuric acid and potassium chloride in acetic anhydride to obtain potassium 3-thianaphthene sulfonate which is then converted to the sulfonyl chloride with $PCl_5$. From the sulfonyl chloride, the thiol is prepared by reduction with zinc dust and sulfuric acid. Reaction of the thiol with chloroacetonitrile yields 3-thianaphthenethioacetonitrile which is then reduced with lithium aluminum hydride to produce 3-thianaphthenethioethylamine, all as described in the Examples hereinafter.

The activity of compounds of the invention process against ventricular fibrillation may be demonstrated in the anti-ventricular fibrillatory pig model and in the ventricular fibrillation threshold-dog model as demonstrated below.

In the basic Anti-Ventricular Fibrillatory Pig Model, compounds are screened in anesthetized pigs. Mean arterial blood pressure and lead II of the EKG is monitored. A mid-line thoracotomy is performed, the heart is exposed and supported in a pericardial cradle. A 4-0 silk suture is placed around the left anterior descending coronary artery (LADCA) just below the circumflex bifurcation. The test compound is administered, e.g. at 10 mg/kg i.v., 10 minutes prior to acute (one-stage) ligation of the LADCA. Mean arterial blood pressure and heart rate are recorded 10 minutes post compound administration. Following acute ligation, the time to ventricular fibrillation is recorded from the EKG. A compound is considered active when 2/2 or 2/3 animals survive acute ligation for 60 minutes. Immediately following survival of acute ligation, the coronary occlusion is released, and blood flow is re-established (reperfusion) to the ischemic area. Compounds which prevent ventricular fibrillation (VF) during the 60 minute acute ligation and the 30 minute reperfusion period will be retested to confirm activity. In establishing the VF model 10/10 pigs (controls) fibrillated within 20 minutes (range 1'05"-19'23") averaging 8'24" following ligation. For standard available anti-arrhythmics evaluated in this model, the dose, and the average time to ventricular fibrillation (n=5 animals/test compound) is as follows:

| Compound | Dose (mg/kg) | | VF Time |
|---|---|---|---|
| Quinindine | 10.0 | | 14'29" |
| Propranolol | 2.5 | | 7'21" |
| Norpace | 10.0 | | 22'49" |
| Verapamil | 1.0 | | 33'14" |
| Procainamide | 50.0 | | 3'0" |
| Lidocaine | 100.0 | mg bolus iv. | 3'34" |
| | 1.0 | mg/kg/min for the | |
| | 10 | minutes before ligation | |
| Nifedipine | 2.5 | | 17'44" |
| Bretylium | 5.0 | | 11'23" |
| Ethmozine | 3.0 | | 1'52" |
| Amiodarone | 10.0 | | 11'46" |
| Aprindine | 5.0 | | 10'39" |
| Tocainide | Infusion only at a rate of 0.75 mg/kg/min for the 10 minutes before ligation | | 8'40" |

The above testing for compounds active against VF was refined as follows. Compounds are screened in anesthetized pigs. Arterial blood pressure and lead II of the EKG are monitored. A mid-line thoracotomy is performed and the heart is exposed and supported in a pericardial cradle. A silk suture is placed around the LADCA just below the circumflex bifurcation and above the septal artery. Mean arterial pressure (MAP) and heart rate (HR) controls are recorded. The test compound (10 mg/kg, iv.) is administered by slow infusion (10 mg/minute). MAP and HR are recorded 1' and 10' post drug infusion. At 10' post infusion, the silk suture around the LADCA is tightened by means of a snare and the time to fibrillation is recorded. This acute (one-stage) ligation of the LADCA is maintained for up to 60'. If the animal survives acute ligation, the LADCA occlusion is released and blood flow is re-established to the ischemic area (reprefusion). If the animal survives a 30' reperfusion, the heart is removed from the chest and is examined to confirm that the ligation was above the septal artery.

Activity is reported as follows:

None=Animal fibrillated sometime during 60' acute ligation

Weak=Animal survived 60' acute ligation but fibrillated sometime during 30' reperfusion Marked=Animal survived 60' acute ligation and 30' reperfusion and ligation was above the septal artery A compound which shows marked activity in 2/2 animals is tested in 2 more animals at the same dose. A dose response is done on any compound which protects at least 3/4 animals from fibrillation and shows weak activity in the remaining animal.

In this refined test, the compounds produced in Examples 1b., 2a., 3, 4, 5, 6 and 7 were tested and all rated as having marked activity at a dose of 10 mg/kg of body weight, i.e., the animal survived the 60 minute ligation and the 30 minute reperfusion.

The Ventricular Fibrillation Threshold-Dog analysis of compounds for activity against ventricular fibrillation may be carried out as described by F. J. Kniffen et al in the Journal of Pharmacology and Experimental Therapeutics, Vol. 192, No. 1, pages 120–128 (1975) and by M. D. Brannan et al in the Abstract entitled "Bepridil (calcium blocker) Increases Ventricular Fibrillation Threshold in Dog Heart", presented at the meeting of FASEB held Apr. 11–15, 1983. In more detail:

Male mongrel dogs weighing between 8 and 14 kg are anesthetized with sodium pentobarbital (30 mg/kg i.v.). They are then intubated and respired with room air at a tidal volume of 30 cc of air/kg of body weight and a rate of 10-12 breaths/minute. The heart is exposed via a left thoracotomy at the fifth intercostal space and suspended in a pericardial cradle. Electrodes are sewn to the heart as follows: an acrylic plaque containing 2 silver-silver chloride electrodes (1 mm diameter, 3 mm apart) is sewn to the surface of the heart in the area of the right ventricular outflow tract for the determination of ventricular fibrillation threshold (VFT). A similar acrylic plaque electrode is sewn in an area of tissue perfused by the left circumflex coronary artery. This electrode is used for the determination of conduction time (CT) and excitation threshold (ET). A bipolar plunge electrode (insulated, stainless steel, 25 gauge, 4 mm long, 2 mm apart) is placed into the interventricular septum for determination of effective refractory period (ERP). Finally, a bipolar plunge electrode is attached via a Grass ear clip to the left atrial appendage for left atrial pacing. The heart is paced at a constant rate (approximately 20 beats/minute above basal heart rate) during measurement of the electrophysiological parameters. Blood pressure via a cannulated carotid artery and lead II EKG are continuously monitored on a Grass model 7 polygraph. Drug infusions are made through a cannulated external jugular vein. For the determination of CT, both the lead II EKG and the ventricular electrogram are displayed at high speed (10 msec/division) on a Tektronix storage oscilloscope and the time between waveforms from the beginning of the Q-wave to the peak of the ventricular electrogram is measured. ET, ERP, and VFT are determined using a Grass S88 stimulator coupled to a stimulus isolation unit (Grass SIU5) and a constant current unit (Grass CCU1A). To determine ET, current is set at its lowest value and single arrhythmic pulses of 0.4 msec duration are delivered 250 msec after ventricular activation (R-spike of the EKG). Current is gradually increased until these delivered pulses evoke a premature ventricular response on the surface EKG. To measure ERP, this current value for ET is doubled and the duration of the pulse is increased to 4 msec to ensure that every delivered pulse will evoke a premature response. The delay between ventricular activation and delivery of an arrhythmic pulse is gradually decreased until the delivered pulse will no longer evoke a premature ventricular response. VFT is determined by delivering a 200 msec train of 4 msec pulses at a frequency of 60 Hz and an intensity of 150 volts. The stimulus is delivered after a delay of 50 msec so that the impulse train scans the T-wave. An increasing amount of current is delivered until the animal fibrillates. At this time defibrillation is accomplished within 15-20 seconds with a defibrillator. After a control determination of all parameters, the test compound is administered by slow infusion (10 mg/minute). The electrophysiological parameters are again measured at 30, 60, 90, and 120 minutes post infusion. At the last VFT determination, if the test compound prevents the animal from fibrillating at the highest deliverable current (44 mA) the train duration is gradually increased until fibrillation occurs.

In the Ventricular Fibrillation Threshold-Dog test, the following results were obtained for various compounds. The results are given in Table 1 for the amount of current (in mA) necessary to initiate ventricular fibrillation before (C) and 30, 60, 90 and 120 minutes after drug administration at a given dosage (in mg/kg of body weight).

TABLE 1

| Compound/dose | C | 30 | 60 | 90 | 120 |
| --- | --- | --- | --- | --- | --- |
| Verapamil/0.33 | 9 | 19 | 16 | 20 | 20 |
| Diltiazem/0.33 | 8 | 15 | 24 | 26 | 21 |
| Nifedipine/0.17 | 7 | 19 | 16 | 13 | 11 |
| Bepridil/5.0 | 6 | 12 | 26* | 22* | 32* |
| Control | 8 | 10 | 10 | 10 | 9 |

*considered statistically significant using Analysis of Variance (ANOVA) and Duncan's Multiple Range ($P < 0.05$)

For compounds used according to the invention processes, Table 2 sets forth the results by Example number which were obtained:

TABLE 2

| Example No./dose | C | 30 | 60 | 90 | 120 |
| --- | --- | --- | --- | --- | --- |
| 1b./5.0 | 11 | 16 | 20 | 18 | 25 |
| 1b./10.0 | 8 | 16 | 27* | 27* | 32* |
| 2a./5.0 | 11 | 20 | 25* | 28* | 31* |
| 2a./10 | 12 | 29* | 32* | 35* | 30* |
| 2b./2.5 | 5 | 15 | 7 | 16 | 17 |
| 2b./5.0 | 10 | 20 | 16 | 25 | 30 |
| 3/5.0 | 8 | 27 | 26 | 24 | 23 |
| 3/10.0 | 6 | 21 | 17 | 11 | 20 |

*considered significant using Analysis of Variance (ANOVA) and Duncan's Multiple Range ($P < 0.05$)

The efficacy of the invention process against ventricular dysrhythmias may be demonstrated in the Harris Ectopy model generally described by A. S. Harris in Circulation, Vol. 1, pages 1318 to 1328 (1950). In particular, male mongrel dogs (Haycock) weighing between 7 and 12 kg were anesthetized with sodium pentobarbital (30 mg/kg, i.v.), intubated, and respired with room air (tidal volume=30 ml/kg; 10-12 breaths/min) with the end of the outflow tube submerged in water to provide respiratory resistance for the lungs once the chest was opened. Under aseptic conditions, the heart was exposed through a left thoracotomy at the fifth intercostal space and suspended in a pericardial cradle. The left anterior descending coronary artery (LADCA) was isolated just below its first diagonal branch. Two silk sutures were placed under the LADCA in preparation for occlusion. A 20-gauge needle was placed over the LADCA, one of the sutures was tied around it, and the needle was immediately withdrawn leaving the LADCA partially occluded. After 20 minutes of partial occlusion, the second suture was tied, completely ligating the LADCA. The chest was then closed, an antibiotic was administered (Combiotic: penicillin and dihydrostreptomycin in aqueous suspension, 1.5 ml, i.m.=300,000 units procaine penicillin G), and the animal was fasted and allowed to recover for 24 hours. On the first day of testing (24 hours post-occlusion) the non-anesthetized animal was placed in a sling and was allowed to stabilize. Lead II electrocardiogram (EKG) was monitored using a Grass Model 7 chart recorder at a paper speed of 5 cm/sec for one-minute control readings. The heart rate and percentage of ectopic beats were recorded. Animals with fewer than 50% ectopic beats were not tested. Animals which qualified for testing were administered test compounds either by slow intravenous infusion (10 mg/minute) or orally by gavage to achieve the dose tested (2.5 and 5.0 mg/kg, i.v.; 10.0 mg/kg, p.o.). EKG recordings were taken at 1 minute post-drug administration and then every 15 minutes up to a maximum of two hours. Four to six animals were tested at each dose and route. The same protocol was followed on the second day of testing (48 hours post-occlusion). Animals with at least 50% ectopic beats received the same dose by the same route as they had received on the previous day of testing. Significance of changes in biological parameters was based on Student's t-test for paired values. Mean values were considered significantly different at the P<0.05 level.

The compound of Example 2b. was tested to determine its intravenous efficacy in reducing ventricular ectopy. The results of testing at 24 hours post-occlusion at two dose levels, 2.5 and 5.0 mg/kg, i.v., are shown in Table 3. The lower dose, 2.5 mg/kg, i.v., transiently decreased heart rate and significantly reduced the number of ventricular arrhythmias (ectopy). At 48 hours post-occlusion, only three of the six animals had greater than 50% ectopy. There was no biologically significant antiarrhythmic effect in these animals. With 5.0 mg/kg, i.v., at 24 hours post-occlusion, the onset of activity was immediate and ectopy remained significantly reduced until 45' post-drug infusion while the decrease in heart rate remained significant until 105' post-drug infusion. At 48 hours post-occlusion, only one animal had greater than 50% ectopy. In this animal, ectopy was immediately reduced and this effect was sustained until 60' post-drug infusion. Of 12 animals tested by intravenous administration, one had emesis (5 mg/kg, i.v.). These results indicate that the compound product of Example 2 in free base or salt form has efficacy as a ventricular antiarrhythmic agent.

The ability of the product of Example 2b. to reduce ventricular ectopy after oral administration was tested at three dose levels, 5.0, 10.0 and 20.0 mg/kg. The results for the 10 mg/kg dose are presented in Table 3. (Only the results from 24 hours post-occlusion appear because none of the animals had greater than 50% ectopy at 48 hours post-occlusion). The lowest dose, 5.0 mg/kg, p.o., had no significant effect on ectopy. At 10.0 mg/kg, p.o., a significant reduction in ectopy occurred from 45' to 105' post-drug administration. Heart rate was significantly reduced from 60' to 120' post-drug administration. This indicated that the efficacy of the compound in reducing ventricular ectopy is not a rate-dependent phenomenon. The highest dose, 20.0 mg/kg, p.o., appeared to produce some atrioventricular conduction distrubances which tended to camouflage the beneficial effect of the drug. The EKG showed a transition from ventricular ectopy to periods of normal sinus rhythm and first degree heart block. One animal died at 60' post-drug administration, apparently from a stroke (the EKG showing no signs of VF or heart failure as the reason for death). This lethality may have been a result of the surgical procedure rather than a drug effect. Of 14 animals tested by oral administration, only one had emesis (20 mg/kg) and one died (20 mg/kg). Thus, the compound product of Example 2 in free base or salt form has oral efficacy as a ventricular antiarrhythmic agent. The results at 10 mg/kg p.o. are shown below in Table 3:

TABLE 3

| | | Time Post-Drug Administration (minutes) | | | | |
|---|---|---|---|---|---|---|
| | | C | 1 | 15 | 30 | 60 | 90 |
| 24 hours post occlusion (N = 6) 2.5 mg/kg i.v. | | | | | | | |
| HR | Mean | 192.3 | 166.3* | 180.5 | 177.8 | 177.8 | 223.7 |
| | S.D. | 12.6 | 6.7 | 23.2 | 16.5 | 22.3 | 86.1 |
| #A | Mean | 181.0 | 95.8* | 161.5 | 170.5 | 167.3 | 217.3 |
| | S.D. | 19.9 | 55.0 | 31.2 | 18.6 | 21.9 | 89.9 |
| %A | Mean | 94.2 | 58.3* | 89.2 | 96.0 | 94.2 | 96.7 |
| | S.D. | 6.7 | 32.0 | 10.6 | 3.6 | 5.8 | 7.2 |

TABLE 3-continued

| | | Time Post-Drug Administration (minutes) | | | | |
|---|---|---|---|---|---|---|
| | | C | 1 | 15 | 30 | 60 | 90 |
| 24 hours post occlusion (N = 6) 5.00 mg/kg i.v. | | | | | | | |
| HR | Mean | 166.5 | 157.8* | 143.2* | 139.7* | 139.0* | 148.8* |
| | S.D. | 15.4 | 11.1 | 19.0 | 16.0 | 24.8 | 18.7 |
| #A | Mean | 139.2 | 32.8* | 23.2 | 60.3* | 93.0 | 114.8 |
| | S.D. | 30.8 | 68.1 | 35.9 | 38.4 | 55.3 | 48.0 |
| %A | Mean | 82.5 | 19.3* | 15.3* | 43.5* | 64.0 | 77.5 |
| | S.D. | 14.1 | 39.3 | 23.4 | 25.1 | 34.2 | 30.3 |
| 24 hours post occlusion (N = 6) 10.00 mg/kg p.o. | | | | | | | |
| HR | Mean | 178.2 | 198.2 | 176.7 | 169.3 | 148.8* | 144.8* |
| | S.D. | 20.3 | 33.8 | 27.6 | 19.7 | 15.8 | 11.3 |
| #A | Mean | 166.2 | 162.5 | 137.2 | 130.5 | 48.7* | 69.2* |
| | S.D. | 30.7 | 84.7 | 77.8 | 65.1 | 45.1 | 54.2 |
| %A | Mean | 92.8 | 80.8 | 75.0 | 75.2 | 31.2* | 46.2* |
| | S.D. | 8.0 | 37.5 | 38.2 | 32.9 | 27.3 | 34.0 |

HR = heart rate
A = number of ectopic beats per minute
%A = percent of ectopic beats per minute
S.D. = standard deviation
* = Statistically Significant (P < 0.05)

The methods of the invention are particularly useful for the treatment of mammals, humans in particular, who have experienced one or more of (i) a myocardial infarction, (ii) ventricular fibrillation, and (iii) abnormal cardiac conduction, e.g. ventricular ectopy. The compounds (I) through (VIII) may be administered immediately after a person experiences a myocardial infarction, ventricular fibrillation, or ventricular ectopy for example in an emergency vehicle transporting a heart attack victim to a hospital. The administration may be oral or parenteral with oral dosages being at about 0.2 to 50 mg/kg of body weight, preferably about 1.0 to 20 mg/kg. Parenteral dosages would be about 0.1 to 25 mg/kg, preferably about 0.5 to 10 mg/kg, for the i.v. route and 0.1 to 50 mg/kg, preferably about 0.5 to 25 mg/kg, for other parenteral routes, e.g., subcutaneously or intramuscularly. In any case, the doseages will be given to the patient about 1 to 4 times per day. In emergencies, the compound may be injected directly into the heart at the i.v. dosage. To prepare the pharmaceutical compositons of this invention one or more compounds of formula (I) to (VIII) or acid addition salts thereof, as the active ingredient is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparation, such as, for example, suspensions, elixirs and solutions, suitable carriers and additives include water, glycols, oils, alcohols, flavoring agents, preservatives, coloring agents and the like; for solid oral preparations such as, for example, powders, capsules, and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. However, for emergency and hospital administration, parenteral administration may be preferred. For parenterals, the carrier will usually comprise sterile water, though other ingredients, for example, for purposes such as aiding solubility or for preservation, may be included. Injectable suspensions or solutions may also be prepared, in which case appropriate liquid carriers, suspending agents and the like may be employed.

In the following examples and throughout the specification the following abbreviations are used: g (grams); ml (milliliters); mg (milligrams); mmoles (millimoles); kg (kilograms); " (minutes); " (seconds); i.v. (intravenous); mm (millimeters); msec (milliseconds); mA (milliamperes); Hz (hertz); TLC (thin layer chromatography); THF (tetrahydrofuran); DMF (dimethyl formamide); and C,H,N,O etc, (the chemical symbols for the elements). Ultraviolet data are given in nanometers with the molar extinction coefficient in parantheses.

EXAMPLE 1 a.  3-[2-(1-Methyl-2-pyrrolidinylideniamino)ethylthio]indole

A solution of 15.9 g (112 mmole) of boron trifluoride etherate in 20 ml anhydrous ether was added slowly with stirring to 7.76 g (84 mmole) of epichlorohydrin in 10 ml anhydrous ether. After 3½ hous of stirring under dry conditions the ether was decanted and the product washed twice with anhydrous diethyl ether and the ether was evaporated with a stream of nitrogen. The product was dissolved in 20 ml of dry $CH_2Cl_2$ and to this was added 8.32 g (84 mmole) of N-methyl-2-pyrrolidone in 20 ml of dry $CH_2Cl_2$. The solution was stirred for six hours under dry conditions and is referred to hereinafter as the Meerwein solution.

A mixture of 16.0 g (70 mmole) of 3-[(2-aminoethyl)-thio]indole hydrochloride in aqueous base was extracted with 250 ml of benzene. The benzene was washed twice with aqueous 1N NaOH, once with brine and dried over anhydrous $K_2CO_3$. The benzene was evaporated in vacuo to give 12.8 g of a red oil of the free base which was dissolved in 45 ml dry $CH_2Cl_2$ and added to the Meerwein solution. The solution was stirred overnight under dry conditions. The resulting brown solution was extracted twice with 50 ml of 20% NaOH, dried over anhydrous $K_2CO_3$ and evaporated in vacuo to yield 18.5 g (97%) of crude brown crystalline 3-[2-(1-methyl-2-pyrrolidinylideneamino)ethylthio]indole. The fumarate salt was made and recrystallized four times, and converted back to free base and recrystallized three more times from isopropanol to give an analytical sample of 4.7 g (25%) of white crystals, mp 143.5°–145.5° C.

Elemental Analysis: Calculated for $C_{15}H_{19}N_3S$: C, 65.89; H, 7.00; N, 15.37 Found: C, 65.83; H, 6.92; N, 15.37.

UV lambda max (methanol): 273(6584), 278(7011) and 287(6358).

b.  3-[2-(1-Methyl-2-pyrrolidinylideneamino)ethylthio]indole hydrochloride

The product of Example 1a. was neutralized with ethereal HCl in methanol and the solvents were evaporated in vacuo. The resulting residue was crystallized from isopropanol, and recrystallized from methanol-isopropanol to give the title compound, mp 158.5°–160.0° C. which was homogeneous by silica gel TLC.

EXAMPLE 2 a.  3-[2-(1-Phenyl-2-pyrrolidinylideneamino)ethylthio]indole (E)-2-butenedioate

A solution of 5.75 g (30 mmole) of 3-(2-aminoethylthio)indole, in 15 ml of dry $CH_2Cl_2$ was added to the Meerwein N-phenylpyrrolidone intermediate in 25 ml of dry $CH_2Cl_2$ prepared from 6.85 g (48 mmole) of boron trifluoride etherate, 3.33 g (36 mmole) of epichlorohydrin and 5.8 g (36 mmole) of N-phenyl-2-pyrrolidinone in a manner analogous to Example 1a. The reaction solution was stirred at room temperature under dry conditions for 40 hours.

To the reaction solution was added an equal volume of $CH_2Cl_2$ and this solution was basified with 50 ml of 1N NaOH. The $CH_2Cl_2$ solution was evaporated and washed once with water, twice with brine and dried over anhydrous $K_2CO_3$. The solution was filtered and evaporated in vacuo to give 11.2 g of viscous oil.

Methanol (50 ml) was added to the crude product causing a white solid to crystallize. To this mixture was added 3.4 g (29 mmole) of fumaric acid which dissolved all solids. This solution was treated with charcoal and filtered and the filtrate was evaporated on a steam bath as about 70 ml of ethyl acetate was added over the next hour. When the solution reached a volume of about 75 ml it was cooled, seeded and scratched and allowed to sit at room temperature for 64 hours. White crystals were then filtered to give 7.5 g (56%) of the title fumarate salt. This salt was recrystallized once from methanol/ethyl acetate, once from methanol/2-propanol and once from methanol/ethyl acetate to give 3.0 g of white crystals, mp 122°–124° C.

Elemental Analysis: Calculated for $C_{20}H_{21}N_3S.5/4C_4H_4O_4$: C, 62.48; H, 5.45; N, 8.74 Found: C, 62.49; H, 5.62; N, 8.64

UV lambda max (methanol): 267(8397), 271(8244), 278(7920), 279(7882), and 288(6622).

b.  3-[2-(1-Phenyl-2-pyrrolidinylideneamino)ethylthio]indole methanesulfonate

The free base of the product of Example 2a. was prepared by treatment of the fumarate with sodium hydroxide and extraction with $CH_2Cl_2$. The free base was dissolved in methanol and neutralized with one equivalent of methanesulfonic acid. The solvents were removed in vacuo to give an orange residue which crystallized upon addition of acetone. The product was recrystallized from acetonitrile/diethyl ether and dried at 25° C. at about 0.5 mm of Hg to give title compound, mp 144.5°–145.5° C.

Elemental Analysis: Calculated for $C_{20}H_{21}N_3S.CH_3SO_3H$: C, 58.45; H, 5.84; N, 9.74 Found: C, 58.42; H, 5.83; N, 9.72

EXAMPLE 3

5-Methoxy-3-[2-(1-methyl-2-pyrrolidinylideneamino)ethylthio]indole

To a solution of 50 g (0.34 mole) of 5-methoxyindole and 25.8 (0.34 mole) of thiourea in 1700 ml of 50% aqueous methanol was added 340 ml of $KI/I_2$ in water over a 5 minute period and the reaction mixture was allowed to stir at room temperature for 3 hours. The reaction mixture was then evaporated in vacuo to about 1100 ml, 68 ml of 50% aqueous NaOH were added under nitrogen, the temperature brought to 85° and the mixture was stirred at 80°–90° for 40 minutes. The mixture was cooled and filtered through glass wool and under nitrogen, 21.2 ml (25.4 g; 0.34 mole) of chloroacetonitrile were added. The reaction was allowed to proceed under $N_2$ for 18 hours after which the reaction mixture was layered over with about 800 ml of diethyl ether and the ether was separated off having dissolved a large portion of suspended solid material. The aqueous solution was extracted three times with 500 ml portions of ether which were combined with the other washings and dried over anhydrous K$_2$CO$_3$. The ether layer was filtered and evaporated in vacuo to 33 g of 5-methoxy-3-cyanomethylthioindole (42% yield) as a tan solid.

To a solution of 30 g (0.13 mole) of the cyanoindole in 1000 ml of anhydrous THF were added dropwise 280 ml of 1 molar BH$_3$ in THF. The mixture was then allowed to stir for 18 hours under a CaCl$_2$ drying tube. To the reaction mixture was slowly added 300 ml of methanol to destroy excess BH$_3$ and stirring was continued for ½ hour. The solvents were evaporated leaving 33 g of a pale green oil which was layered over with water and extracted three times with 600 ml portions of CH$_2$Cl$_2$. The CH$_2$Cl$_2$ was dried over anhydrous K$_2$CO$_3$ and evaporated in vacuo to give 29 g of a pale green oil which was suspended in about 500 ml of aqueous HCl (5%) and extracted with CH$_2$Cl$_2$. The water solution was made alkaline with 6 normal NaOH and extracted with CH$_2$Cl$_2$. The CH$_2$Cl$_2$ extract was dried over anhydrous K$_2$CO$_3$. This was filtered and evaporated to a dark oil which upon standing gave 21 g (72%) of 5-methoxy-3-aminoethylthio indole as tan crystals.

To a solution of 21.4 g of BF$_3$ diethylester complex in 50 ml anhydrous ether was added dropwise 11 g of epichlorohydrin in 50 ml of anhydrous ether. The mixture was allowed to stir for 18 hours under a CaCl$_2$ drying tube after which the ether was decanted and the residue washed three times with 50 ml portions of anhydrous ether. The residue was dried under a nitrogen stream leaving fluffy white crystals which were dissolved in 50 ml of anhydrous CH$_2$Cl$_2$ and 11.2 g of N-methylpyrrolidone in 50 ml anhydrous CH$_2$Cl$_2$ were added. This mixture was allowed to stir under a CaCl$_2$ tube for 4½ hours.

To a suspension of 21 g (0.89 mole) of the crude aminoindole in 50 ml of anhydrous CH$_2$Cl$_2$ was added the above-described Meerwein mixture. The reaction mixture was allowed to stir for 18 hours, washed twice with 250 ml portions of 20% aqueous NaOH and once with saturated NaCl solution. The CH$_2$Cl$_2$ solution was dried over anhydrous K$_2$CO$_3$ and evaporated to give 35 g of a tan solid. Trituration with acetone gave 23 g (85% yield) of a near-white crystalline product. The title product was recrystallized from methanol/acetone, mp 154°–157° C.

UV lamda max: 277(5844); 296(5254); 307(4357)

EXAMPLE 4

3-[2-(1-Methyl-2-pyrrolidinylideneamino)ethylthio]7-methylindole cyclohexylsulfamate A mixture was prepared from 24.1 g (184 mmole) of 7-methylindole, 15.4 g (202 mmole) of thiourea and 195 ml of a one normal KI/I$_2$ solution in 150 ml of methanol and stirred for 75 minutes. The solution was evaporated in vacuo and 400 ml of 1.5 nomral NaOH was added under N$_2$. The solution was heated to 80°–90° C. for 20 minutes under N$_2$. The solution was cooled and extracted twice with ether, layered over with ether and 11.8 ml (184 mmole) of chloroacetonitrile was added. The solution was stirred for 10 hours under N$_2$ at room temperature.

The ether solution was separated and dried over MgSO$_4$. The filtered solution was evaporated in vacuo to give 24.4 g (66%) of 7-methylindol-3-ylthioacetonitrile as a tan solid. An ether solution of 14.1 g (70 mmole) of the nitrile was treated with 2.7 g (70 mmole) of lithium aluminum hydride and 9.5 g (70 mmole) of AlCl$_3$. The dried ether solution was evaporated in vacuo to give 3-[(2-aminoethyl)thiol]-7-methylindole which was crystalized from isopropanol to give 6.2 g of tan crystals.

The amine was dissolved in 20 ml of dry CH$_2$Cl$_2$ and added to the Meerwein-pyrrolidone intermediate prepared as described in Example 1a from 6.85 g (48 mmole) of BF$_3$. etherate, 3.33 g (36 mmole) of epichlorohydrin and 3.50 g (36 mmole) of N-methyl-2-pyrrolidone. The solution was stirred at room temperature and under dry conditions for 40 hours.

The solution was basified with 40 ml of normal NaOH and washed once with H$_2$O, once with brine and dried over anhydrous K$_2$CO$_3$. The filtered solution was evaporated in vacuo to give 10.1 g of crystalline product.

The corresponding cyclohexamate salt was crystallized from isopropanol/diethyl ether by addition of 5.0 g of cyclohexylsulfamic acid to a solution of the amine in methanol and subsequently displacing the methanol by heating and the addition of isopropanol to yield 9.8 g of white crystals, mp 130.5°–134° C. This salt was recrystallized from chloroform/ethyl acetate, methanol-/isopropanol, methanol/acetone, chloroform/ethyl acetate and finally from ethanol/ether to give 5.4 g of analytically pure white crystals, mp 152.5°–154.5° C.

Elemental Analysis: Calculated for C$_{16}$H$_{21}$N$_3$S.C$_6$H$_{13}$NO$_3$S: C, 56.62; H, 7.34; N, 12.01 Found: C, 56.50; H, 7.36; N, 11.93

UV lambda max (methanol): 272(6662), 278(6863) and 288(5608)

EXAMPLE 5

5-Chloro-3-[2-(1-methyl-2-pyrrolidinylideneamino)ethylthio]-2-methylindole saccharinate A slurry of 2.80 g (0.0116 mole) of 2-[(5-chloro-2-methyl-1H-indol-3-yl)thio]ethamamine in 50 ml of dry CH$_2$Cl$_2$ was added to the pyrrolidone-Meerwein intermediate in 11 ml of dry CH$_2$Cl$_2$ generated from 1.10 ml (0.014 mole) of epichlorohydrin, 2.67 g (0.0188 mole) of boron trifluoride etherate and 1.39 g (0.014 mole) of N-methyl-2-pyrrolidone. After 4 days of stirring at room temperature, 20 ml of CH$_2$Cl$_2$ was added and the reaction mixture was extracted with a 0.67 normal NaOH solution. The organic layer was extracted with one normal aqueous NaOH, dried over K$_2$CO$_3$, filtered and evaporated in vacuo to give 2.4 g of a solid. An additional 1.4 g of product was obtained by repeating the extraction of the aqueous layer. Mixing 3.81 g of crude product and 2.26 g of saccharin in methanol/isopropanol gave 4.95 g of the saccharinate salt. Recrystallization from methanol/isopropanol gave 4.77 g (81%) of a white crystalline solid, mp 158.5°–160.5° C.

Elemental Analysis: Calculated for C$_{16}$H$_{20}$ClN$_3$S.C$_7$H$_5$NO$_3$S: C, 54.69; H, 5.00; N, 11.09 Found: C, 54.71; H, 5.01; N, 11.09

EXAMPLE 6

2-[(3-Benzo[b]thienyl)thio]-N-(1-methyl-2-piperidinylidene)ethanamine monoperchlorate To a cooled solution of 50.0 g (0.373 mole) of thianaphthene and 49.85 g (0.488 mole) of acetic anhydride was added dropwise 21.75 ml of concentrated H$_2$SO$_4$ (0.41 mole) keeping the temperature below 15° C. The mixture was stirred at 20° C. for 2½ hours and mixed with 300 ml of ice-water, washed twice with 260 ml portions of diethyl ether. The aqueous layer was treated with about 300 ml of a hot saturated aqueous solution of 99.9 g (1.34 mole) of KCl. Filtration and recrystallization with 95% ethanol yielded 58.1 g (61.57%) of potassium 3-thianaphthene sulfonate.

The corresponding sulfonyl chloride was produced by first reacting 55 g of the salt neat with 65.9 g (0.32 mole) of PCl$_5$. After 1 hour of stirring, the reaction mixture was evaporated in vacuo and the residue was mixed with ice and extracted twice with anhydrous diethyl ether. The ether layer was washed with cold water, dried with MgSO$_4$ and evaporated to a solid which was recrystallized from hexane to give 47.3 g (93%) of 3-thianaphthene sulfonyl chloride, mp 86°–88° C.

To 22.5 g (0.097 mole) of the chloride was added 59.27 (0.604 mole) of concentrated H$_2$SO$_4$ in 167 g of ice and the mixture was stirred while 20.7 g (0.317 mole) of Zn dust was added in small portions at −5° C. The mixture was then warmed to 65° C., and stirred under N$_2$ overnight. The cooled reaction mixture was then extracted with diethyl ether, dried with anhydrous K$_2$CO$_3$ and evaporated to an oil which was dissolved in toluene and evaporated in vacuo to yield 12 g (74%) of 3-thianaphthenethiol as a yellow oil. The oil was dissolved in DMF (dry) and was kept under N$_2$.

To 9.7 g (0.05 mole) of the thiol in 24 ml of DMF was added 2.4 g (0.06 mole) of sodium hydroxide and the mixture was warmed to 65° C. after which 5 g (0.066 mole) of chloroacetonitrile in 5 ml of DMF was added continuously. The mixture was then stirred at room temperature for 65 minutes after which 150 ml of water were added and the mixture was extracted with diethyl ether, dried with anhydrous K$_2$CO$_3$ and evaporated in vacuo to yield 9.3 g (78%) of 3-thianaphthenethioacetonitrile as a brown oil.

To a stirring suspension of 5.07 g (0.13 mole) of lithium aluminum hydride in 150 ml of diethylether under N$_2$ was dropwise added 9.0 g (0.043 mole) of the acetonitrile in 100 ml of anhydrous diethyl ether and the reaction mixture was stirred overnight after which 5.5 ml of cold water was added a cautiously to the mixture, followed by 5.5 ml of 15% NaOH and finally 16.5 ml of cold water. The mixture was stirred for an additional 20 minutes, extracted with diethyl ether and the ether extracts were washed with normal NaOH, and a saturated solution of NaCl, dried with anhydrous K$_2$CO$_3$ and evaporated in vacuo to give 6.7 g of 3-thianaphthenethioethylamine as a thick yellow oil.

A solution of 2 g of the amine in 5 ml of dry CH$_2$Cl$_2$ was added dropwise to the Meerwein-piperidone intermediate prepared as described in Example 1a. from 2.19 g (0.015 mole) of boron trifluoride etherate, 0.96 ml (0.0115 mole) of epichlorohydrin and 1.3 g (0.0115 mole) of N-methyl-2-piperidone in 8 ml of dry CH$_2$Cl$_2$. The mixture was stirred under anhydrous conditions for over 24 hours, after which it was basified with normal NaOH, extracted with CH$_2$Cl$_2$, washed with water, followed by saturated NaCl, dried with anhydrous K$_2$CO$_3$ and vacuum evaporated to a brown oil to which was added anhydrous diethyl ether and acidified with HClO$_4$. The filtered perchlorate salt was recrystallized twice from methanol/acetone/diethylether to yield 1.17 g of the title product as a light tan solid, mp 178°–180° C.

Elemental Analysis: Calculated for C$_{16}$H$_{20}$N$_2$S$_2$.HClO$_4$: C, 47.46; H, 5.23; N, 6.92 Found: C, 47.40; H, 5.25; N, 6.90

EXAMPLE 7

2-[(3-Benzo[b]thienyl)thio]-N-(1-methyl-2-pyrrolidinylidene)ethanamine (E)-2-butenedioate A solution of 2.2 g of 3-thianaphthenethioethylamine dissolved in dry CH$_2$Cl$_2$ was added dropwise to the Meerwein pyrrolidone intermediate prepared as described in Example 1a. from 2.44 g of boron trifluoride etherate in 9 ml of anhydrous diethylether, 1.0 ml of epichlorohydrin in 6.8 ml of ether, and 1.27 g of N-methyl-2-pyrrolidone in 4.9 ml of dry CH$_2$Cl$_2$. The mixture was stirred under anhydrous conditions overnight after which it was diluted with an additional 30 ml of CH$_2$Cl$_2$ and basified with 32 ml of 0.67 normal sodium hydroxide, extracted with CH$_2$Cl$_2$, washed with water, saturated brine, dried over anhydrous K$_2$CO$_3$, and evaporated in vacuo to yield 2.5 g of crude 2-[(3-benzo[b]thienyl)thio)-N-(1-methyl-2-pyrrolidinylidene)ethanamine.

The crude free base was dissolved in acetone and treated with a solution of one equivalent of fumaric acid in a mixture of methanol and acetone. Diethyl ether was added to precipitate 2.65 g of crude fumarate salt. Recrystallization from a 1:1 mixture of methanol and acetone/ether afforded 1.7 g of pure 2-[(3-benzo[b]-thienyl)thio]-N-(1-methyl-2-pyrrolidinylidene)-ethanamine (E)-2-butenedioate as a white solid, mp 122.5°–124.5° C.

Elemental Analysis: Calculated for C$_{15}$H$_{18}$N$_2$S$_2$.C$_4$H$_4$O$_4$: C, 56,13; H, 5.46; N, 6.89 Found: C, 55.98; H, 5.51; N, 6.82

EXAMPLE 8

2-[(3-Benzo[b]thienyl)thio]-N-(1-phenyl-2-pyrrolidinylidene)ethanamine

The procedure of Example 7 may be repeated using the Meerwein reagent of N-phenyl-2-pyrrolidinone prepared in Example 2a. in the place of the N-methyl compound. The product of the reaction is the title compound.

What is claimed is:

1. A method of preventing ventricular fibrillation in a mammal, which comprises administering to the mammal, an effective amount of a thioheterocyclic selected from the group consisting of:

3-[2-(1-methyl-2-pyrrolidinylideneamino)ethylthio]indole;

3-[2-(1-phenyl-2-pyrrolidinylideneamino)ethylthio]indole;

5-methoxy-3-[2-(1-methyl-2-pyrrolidinylideneamino)ethylthio]indole;

3-[2-(1-methyl-2-pyrrolidinylideneamino)ethylthio]-7-methylindole;

5-chloro-3-[2-(1-methyl-2-pyrrolidinylideneamino)ethylthio]-2-methylindole;

2-[(3-benzo[b]thienyl)thio]-N-(1-methyl-2-piperidinylidene)ethanamine; or

2-[(3-benzo[b]thienyl)thio]-N-(1-methyl-2-pyrrolidinylidene)ethanamine;

and the pharmaceutically-acceptable acid-addition salts thereof.

2. The method of claim 1, wherein said thioheterocyclic is 3-[2-(1-methyl-2-pyrrolidinylideneamino)ethylthio]indole.

3. The method of claim 1, wherein said thioheterocyclic is 3-[2-(1-phenyl-2-pyrrolidinylideneamino)ethylthio]indole.

4. The method of claim 1, wherein said thioheterocyclic is 5-methoxy-2-[2-(1-methyl-2-pyrrolidinylideneamino)ethylthio]indole.

5. The method of claim 1, wherein said thioheterocyclic is 3-[2-(1-methyl-2-pyrrolidinylideneamino)ethylthio]-7-methylindole.

6. The method of claim 1, wherein said thioheterocyclic is 5-chloro-3-[2-(1-methyl-2-pyrrolidinylideneamino)ethylthio]-2-methylindole.

7. The method of claim 1, wherein said thioheterocyclic is 2-[(3-benzo[b]thienyl)thio]-N-(1-methyl-2-piperidinylidene)ethanamine.

8. The method of claim 1, wherein said thioheterocyclic is 2-[(3-benzo[b]thienyl)thio]-N-(1-methyl-2-pyrrolidinylidene)ethanamine.

9. The method of claim 1, wherein said mammal is a human.

10. The method of claim 9, wherein said human has a history of one or more of:

(i) a myocardial infarction;
(ii) ventricular fibrillation; or
(iii) abnormal cardiac conduction.

11. The method of claim 9, wherein said thioheterocylic is administered immediately after the human experiences a myocardial infarction.

12. The method of claim 1, wherein said thioheterocyclic is administered 2 to 4 times per day.

13. The method of claim 1, wherein said thioheterocyclic salts are salts made with acids selected from the group consisting of hydrochloric, hydrobormic, hydroiodic, perchloric, sulfuric, nitric, a phosphoric, acetic, propionic, glycolic, lactic, pyruvic, malonic, succinic, maleic, fumeric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicyclic, p-aminosalicyclic, 2-phenoxybenzoic, 2-acetoxybenzoic or a salt made with saccharin.

* * * * *